US011484643B2

(12) United States Patent
Montalvo et al.

(10) Patent No.: US 11,484,643 B2
(45) Date of Patent: Nov. 1, 2022

(54) AMBULATORY INFUSION DEVICES AND FILTER ASSEMBLIES FOR USE WITH SAME

(71) Applicant: MEDTRONIC MINIMED, INC., Minneapolis, MN (US)

(72) Inventors: Susan McConnell Montalvo, Woodland Hills, CA (US); Charles L. Byers, Canyon Country, CA (US); Rudolph A. Montalvo, Woodland Hills, CA (US); Milton Stott, Camarillo, CA (US); Darren Y. K. Yap, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 183 days.

(21) Appl. No.: 16/888,744

(22) Filed: May 31, 2020

(65) Prior Publication Data
US 2020/0390970 A1    Dec. 17, 2020

Related U.S. Application Data

(63) Continuation of application No. 15/823,278, filed on Nov. 27, 2017, now Pat. No. 10,675,403.
(Continued)

(51) Int. Cl.
*A61M 5/142* (2006.01)
*A61M 5/165* (2006.01)
(Continued)

(52) U.S. Cl.
CPC ........ *A61M 5/14244* (2013.01); *A61M 5/145* (2013.01); *A61M 5/14248* (2013.01);
(Continued)

(58) Field of Classification Search
CPC ............ A61M 5/1407; A61M 5/14244; A61M 5/145; A61M 5/165; A61M 2005/1406;
(Continued)

(56) References Cited

U.S. PATENT DOCUMENTS 2,248,006 A    7/1941 MacCallum
4,395,260 A    7/1983 Todd et al.
(Continued)

FOREIGN PATENT DOCUMENTS

EP    142866 A2    5/1985
EP    0586740 A1   3/1994
(Continued)

OTHER PUBLICATIONS

PCT International Search and Written Opinion dated Feb. 21, 2018 for PCT App. Ser. No. PCT/US2017/063308.
(Continued)

*Primary Examiner* — Jason E Flick
(74) *Attorney, Agent, or Firm* — Foley & Lardner LLP

(57) ABSTRACT

An ambulatory infusing device including a housing, a reservoir defining an interior volume, a wall associated with the housing and having an inner surface that faces into the reservoir interior volume, and a filter assembly. The filter assembly may include a filter assembly housing with a housing filter portion having a free end associated with the inner surface of the wall and a filter supporting volume that extends to the free end of the housing filter portion, and a filter located within the filter supporting volume that extends to at least the free end of the housing filter portion.

17 Claims, 7 Drawing Sheets

Related U.S. Application Data

(60) Provisional application No. 62/452,637, filed on Jan. 31, 2017.

(51) Int. Cl.
*A61M 5/145* (2006.01)
*A61M 5/38* (2006.01)
*A61M 5/36* (2006.01)
*A61M 5/14* (2006.01)
*A61M 5/168* (2006.01)
*A61M 5/158* (2006.01)

(52) U.S. Cl.
CPC .............. *A61M 5/165* (2013.01); *A61M 5/36* (2013.01); *A61M 5/38* (2013.01); *A61M 5/1407* (2013.01); *A61M 5/14212* (2013.01); *A61M 5/158* (2013.01); *A61M 5/16854* (2013.01); *A61M 2005/1406* (2013.01); *A61M 2205/18* (2013.01)

(58) Field of Classification Search
CPC .......... A61M 2205/18; A61M 5/14212; A61M 5/14248; A61M 5/158; A61M 5/16854; A61M 5/36; A61M 5/38; A61M 5/14; A61M 5/142; A61M 5/14276; A61M 2005/14513; A61M 5/14586; A61M 5/14593; A61M 2005/1657; A61M 5/14224; A61M 5/16831; A61M 5/365
See application file for complete search history.

(56) References Cited

U.S. PATENT DOCUMENTS

| | | | |
|---|---|---|---|
| 4,573,994 A | 3/1986 | Fischell et al. | |
| 4,714,462 A | 12/1987 | DiDomenico | |
| 4,718,893 A | 1/1988 | Dorman et al. | |
| 4,743,371 A | 5/1988 | Servas | |
| 4,772,263 A | 9/1988 | Dorman et al. | |
| 4,838,887 A | 6/1989 | Idriss | |
| 4,955,861 A | 9/1990 | Energren et al. | |
| 5,088,983 A | 2/1992 | Burke | |
| 5,417,663 A * | 5/1995 | Slettenmark | A61M 5/14276 604/126 |
| 5,471,663 A | 5/1995 | Slettenmark | |
| 5,957,890 A | 9/1999 | Mann et al. | |
| 6,361,780 B1 * | 3/2002 | Ley | A61M 31/002 424/443 |
| 8,740,861 B2 | 6/2014 | McConnell et al. | |
| 10,668,209 B2 | 6/2020 | Montalvo et al. | |
| 10,675,403 B2 | 6/2020 | Montalvo et al. | |
| 2002/0087147 A1* | 7/2002 | Hooper | A61M 5/141 604/892.1 |
| 2009/0264870 A1 | 10/2009 | Christenson | |
| 2010/0274196 A1 | 10/2010 | Brandt et al. | |
| 2011/0190688 A1 | 8/2011 | Tagliaferri et al. | |
| 2014/0228806 A1 | 8/2014 | Alisantoso et al. | |
| 2016/0095987 A1* | 4/2016 | Chattaraj | A61M 5/14244 604/126 |
| 2018/0214633 A1 | 8/2018 | Montalvo et al. | |
| 2020/0297923 A1 | 9/2020 | Montalvo et al. | |

FOREIGN PATENT DOCUMENTS

| | | |
|---|---|---|
| EP | 0790070 A1 | 8/1997 |
| WO | WO-96/40357 A1 | 12/1996 |

OTHER PUBLICATIONS

Extended European Search Report dated Nov. 23, 2021, from application No. 21199566.7.
US Non-Final Office Action dated Feb. 16, 2022, from U.S. Appl. No. 16/888,749.
U.S. Notice of Allowance dated May 26, 2022, from U.S. Appl. No. 16/888,749.

* cited by examiner

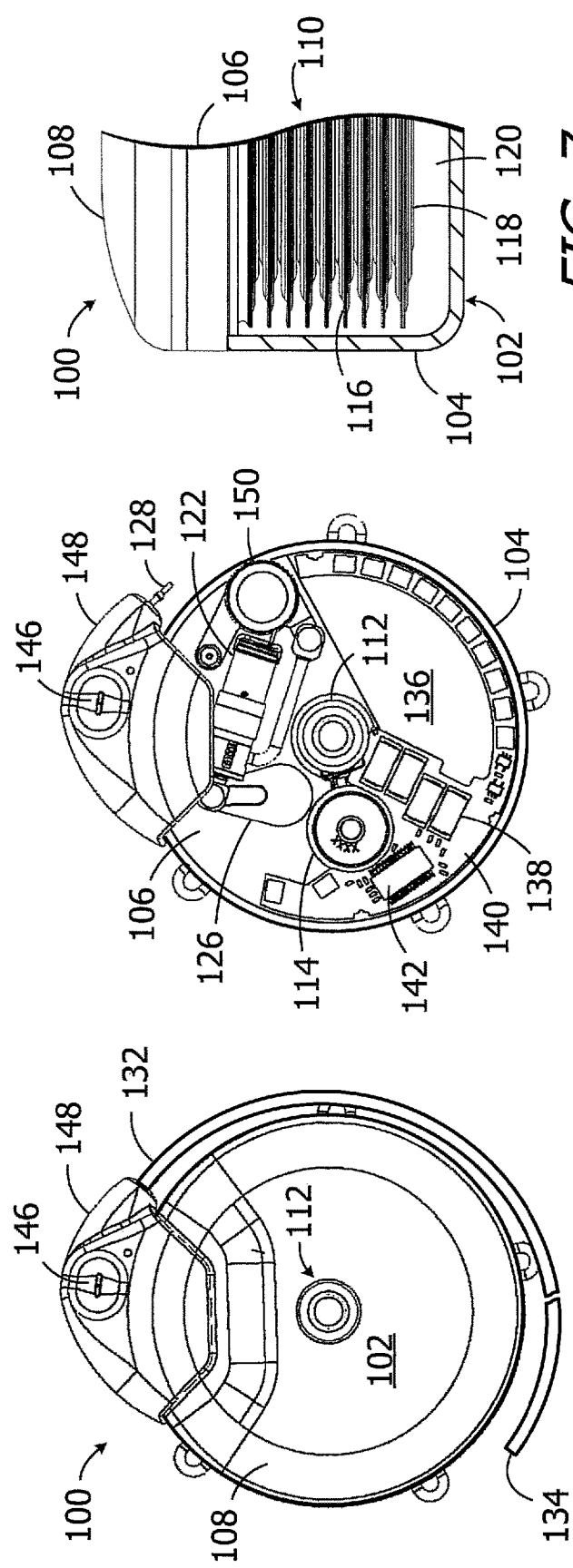
FIG. 5
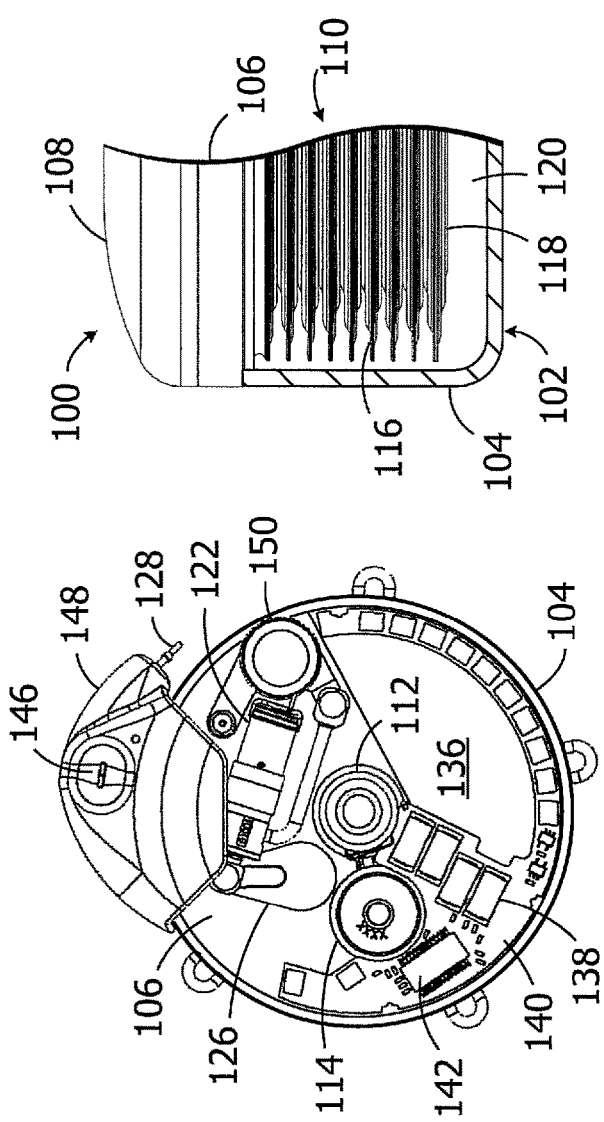
FIG. 6
FIG. 7
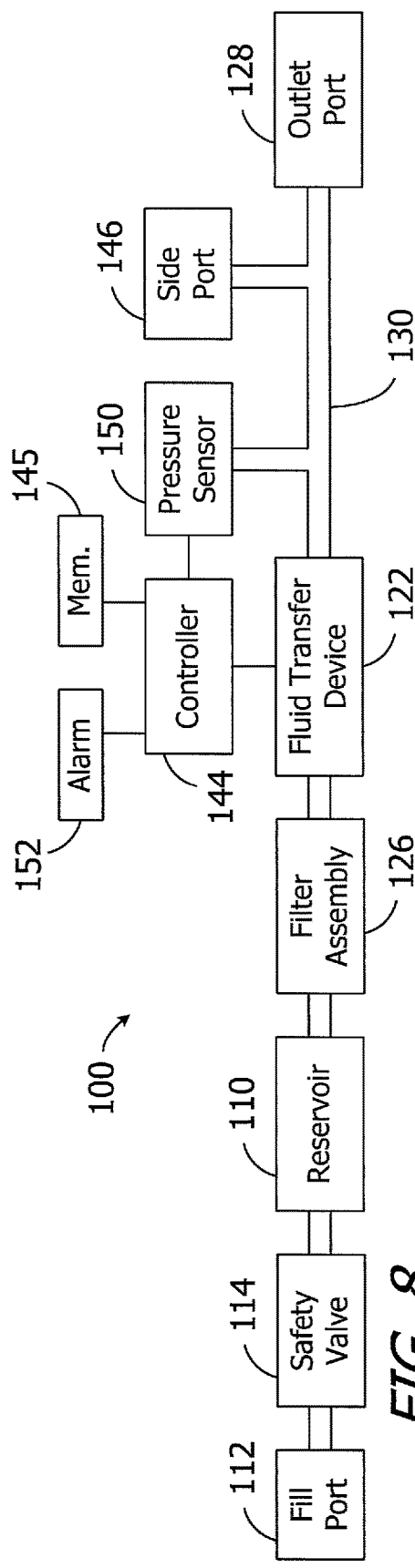
FIG. 8

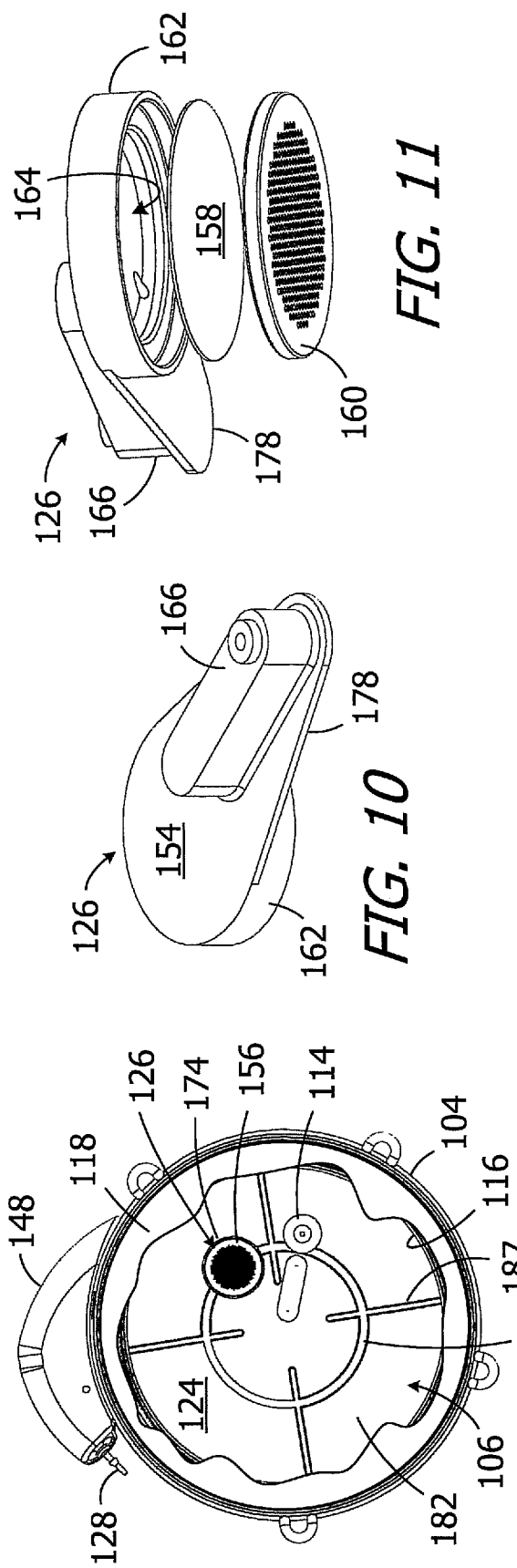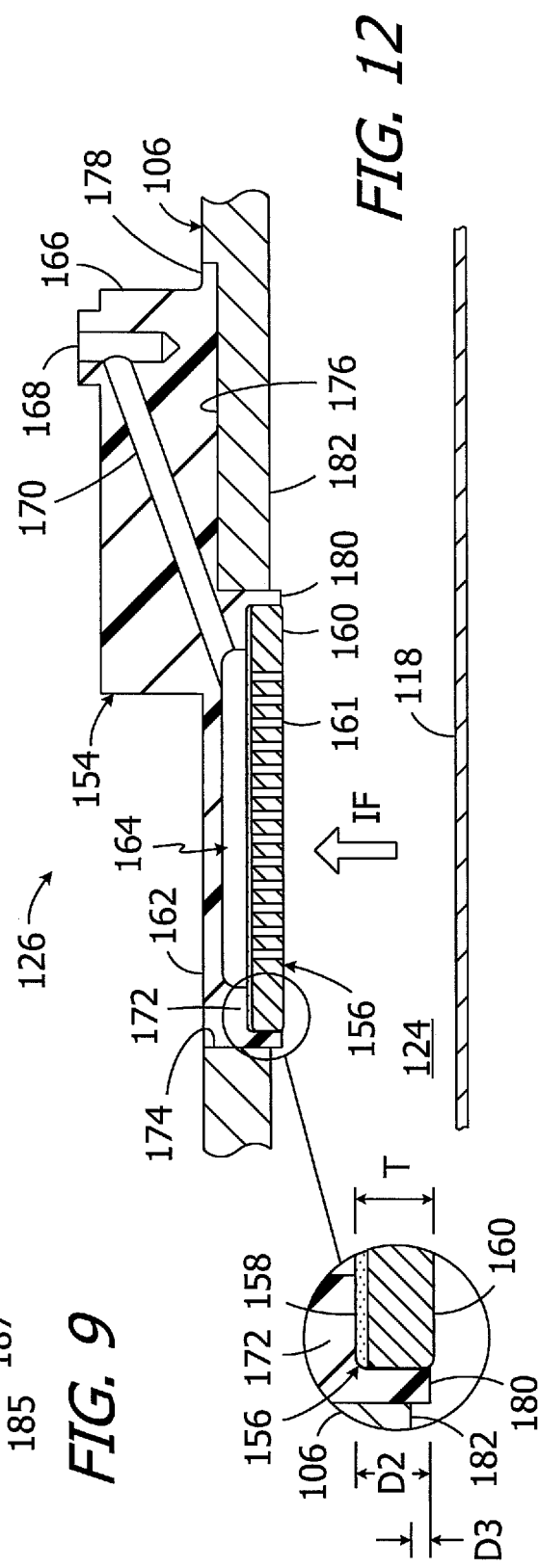

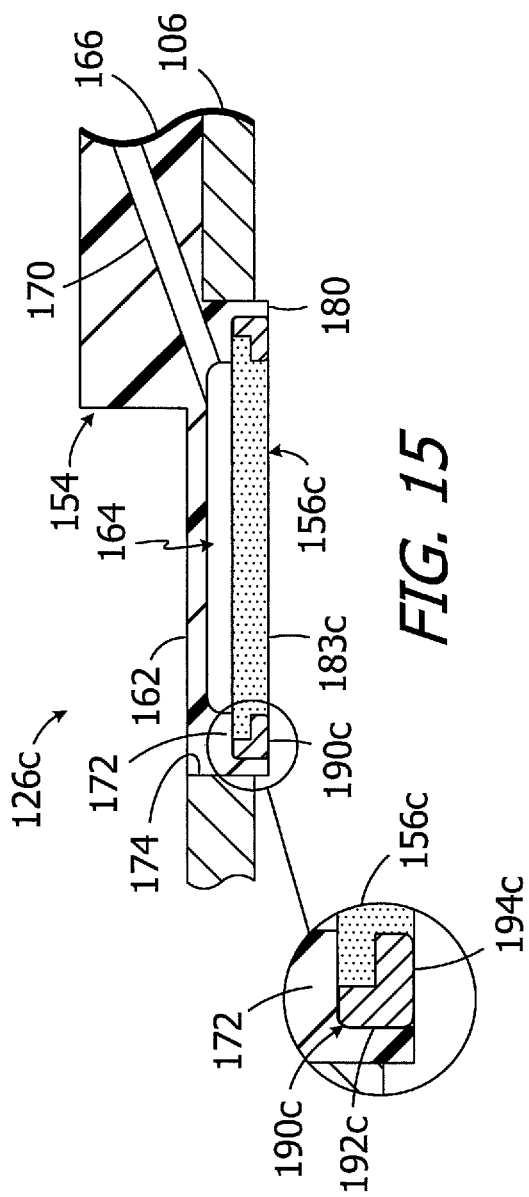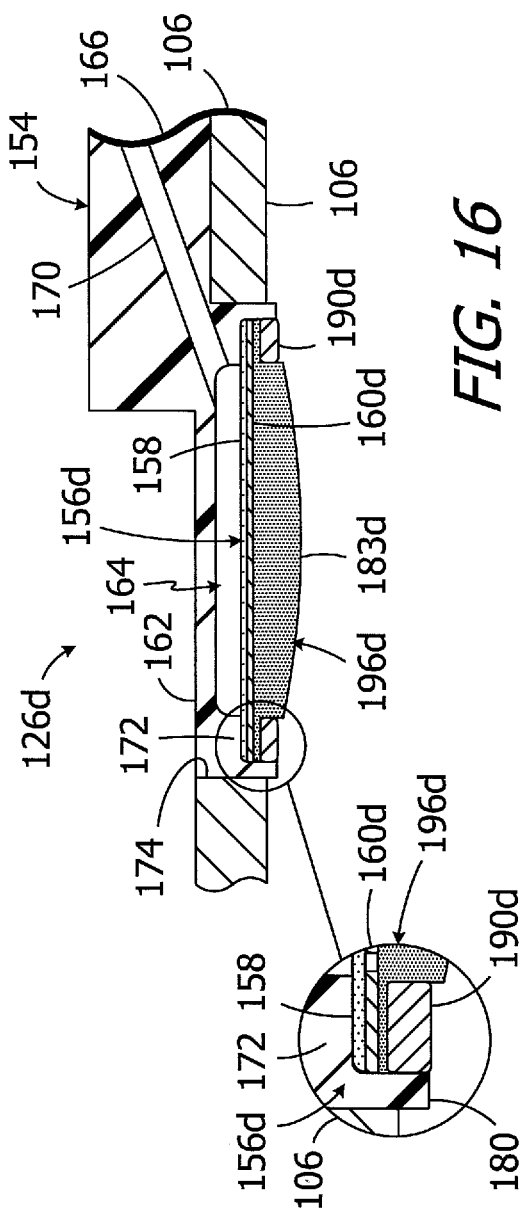

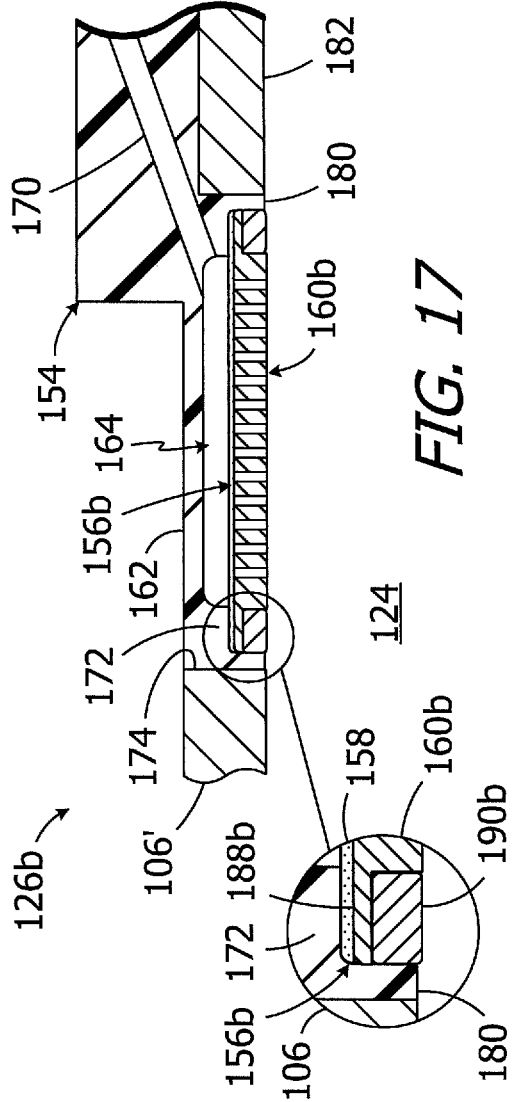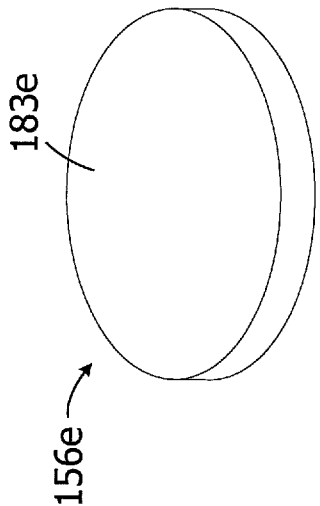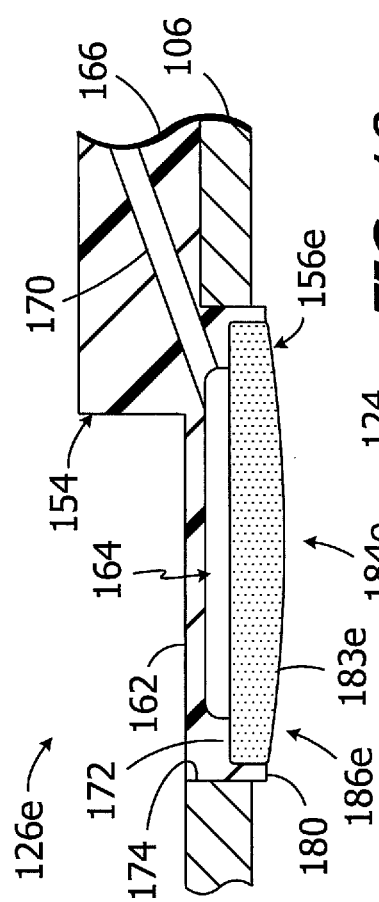

AMBULATORY INFUSION DEVICES AND FILTER ASSEMBLIES FOR USE WITH SAME

CROSS-REFERENCE TO RELATED APPLICATION

This application is a continuation of U.S. application Ser. No. 15/823,278, filed Nov. 27, 2017, now U.S. Pat. No. 10,675,403, which claims the benefit of U.S. Provisional Application No. 62/452,637, filed Jan. 31, 2017, which is incorporated herein by reference.

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") in accordance with a delivery profile that specifies one or more flow rates during the delivery profile cycle, and frequently include a reservoir and a fluid transfer device. The reservoir is used to store the infusible substance and is coupled to the fluid transfer device which is, in turn, connected to an outlet port. A catheter, which has at least one outlet at the target body region, may be connected to the outlet port. As such, infusible substance in the reservoir may be transferred from the reservoir to the target body region by way of the fluid transfer device and catheter.

SUMMARY

An infusion device in accordance with at least one of the present inventions includes a housing, a reservoir defining an interior volume, a wall associated with the housing and having an inner surface that faces into the reservoir interior volume, and a filter assembly. The filter assembly may include a filter assembly housing with a housing filter portion having a free end associated with the inner surface of the wall and a filter supporting volume that extends to the free end of the housing filter portion, and a filter located within the filter supporting volume that extends to at least the free end of the housing filter portion. There are a variety of advantages associated with such an infusion device. By way of example, but not limitation, a filter that extends to at least the free end of the housing filter portion eliminates the above-described bubble trap. As such, the infusion device will be functionally effective when there are air bubbles in the infusible substance.

BRIEF DESCRIPTION OF THE DRAWINGS

Detailed descriptions of exemplary embodiments will be made with reference to the accompanying drawings.

FIG. 5 is a front view of an implantable infusion device in accordance with one embodiment of a present invention.
FIG. 6 is a front view of the implantable infusion device illustrated in FIG. 5 with the housing cover removed.
FIG. 7 is a side, partial section view of a portion of the implantable infusion device illustrated in FIG. 5.
FIG. 8 is a block diagram of the implantable infusion device illustrated in FIG. 5.
FIG. 9 is a rear, cutaway view of the implantable infusion device illustrated in FIG. 5 with the housing bottom portion removed.
FIG. 10 is a perspective view of the filter assembly in the implantable infusion device illustrated in FIG. 5.
FIG. 11 is an exploded perspective view of the filter assembly in the implantable infusion device illustrated in FIG. 5.
FIG. 12 is a section view of a portion of the implantable infusion device illustrated in FIG. 5.
FIG. 15 is a section view of a portion of an implantable infusion device in accordance with one embodiment of a present invention.
FIG. 16 is a section view of a portion of an implantable infusion device in accordance with one embodiment of a present invention.
FIG. 17 is a section view of a portion of an implantable infusion device in accordance with one embodiment of a present invention.
FIG. 18 is a section view of a portion of an implantable infusion device in accordance with one embodiment of a present invention.
FIG. 19 is a perspective view of a filter in accordance with one embodiment of a present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions have application in a wide variety of apparatus. One example is an electromagnet-pump-based fluid transfer device that may be employed in an implantable infusion device. The present inventions are not, however, limited to electromagnet-pump-based fluid transfer devices and implantable infusion devices and are instead also applicable to other fluid transfer devices and infusion devices that currently exist, or are yet to be developed. For example, the present inventions are applicable to fluid transfer devices with solenoid pumps or any other pump that delivers a known and non-adjustable volume into a compliant volume.

Figure 2:
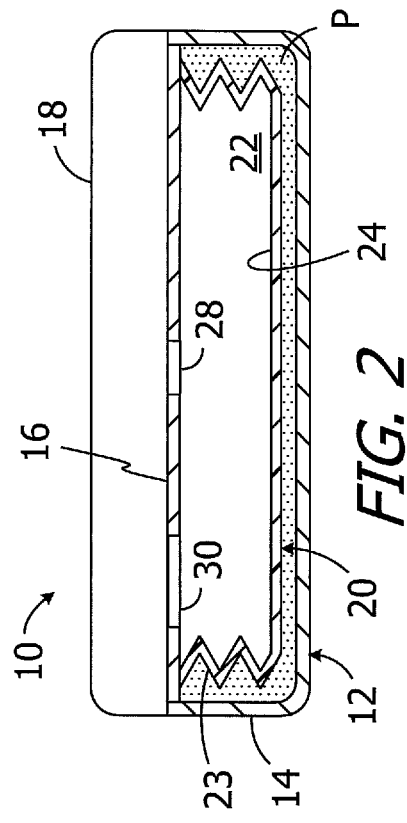
FIG. 2 is a partial section view taken along line 2-2 in FIG. 1.
Figure 1:
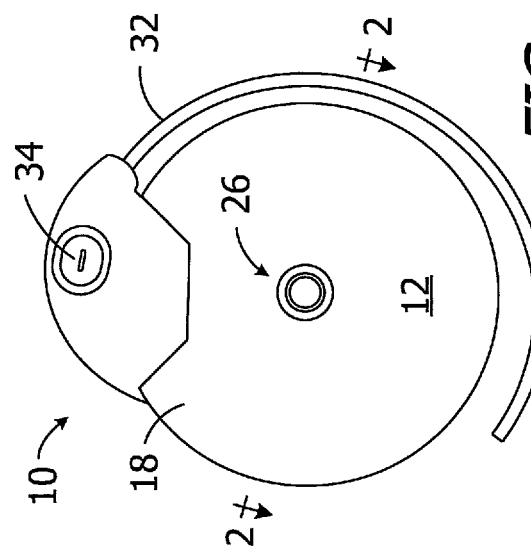
FIG. 1 is a front view of an implantable infusion device.

One example of an infusion device is illustrated in FIGS. 1 and 2. The infusion device 10 includes a housing 12 (e.g. a titanium housing) with a bottom portion 14, an internal wall 16, and a cover 18. A reservoir 20 is located within the housing bottom portion 14 and an infusible substance (e.g. medication) may be stored in the reservoir internal volume 22. A wide variety of reservoirs may be employed. In the illustrated embodiment, the reservoir 20 is in the form of a titanium bellows, with convolutes 23 and an end wall 24, that is positioned within a sealed volume defined by the housing bottom portion 14 and internal wall 16. The remainder of the sealed volume is occupied by propellant P, which may be used to exert negative pressure on the reservoir 20. The reservoir 20 may be replenished by way of a fill port 26 that extends through the housing cover 18 and is connected to a reservoir inlet 28. A hypodermic needle (not shown), which is configured to be pushed through the fill port 26, may be used to replenish the reservoir 20. A safety valve (not shown) that is configured to close when the pressure within the internal volume 22 reaches a predetermined level may be located between the fill port 26 and the reservoir inlet 28. The fluid transfer device and various electronic components (not shown) are located within a sealed volume defined by the housing internal wall 16 and cover 18. The inlet of the fluid transfer device is coupled to the reservoir internal volume 22 by way of a filter assembly 30 that blocks pathogens and precipitates which may be in the infusible substance. The outlet of the fluid transfer device is operably connected to a catheter 32. Access to the catheter 32 may also be obtained by way of a catheter access port 34.

Figure 4:
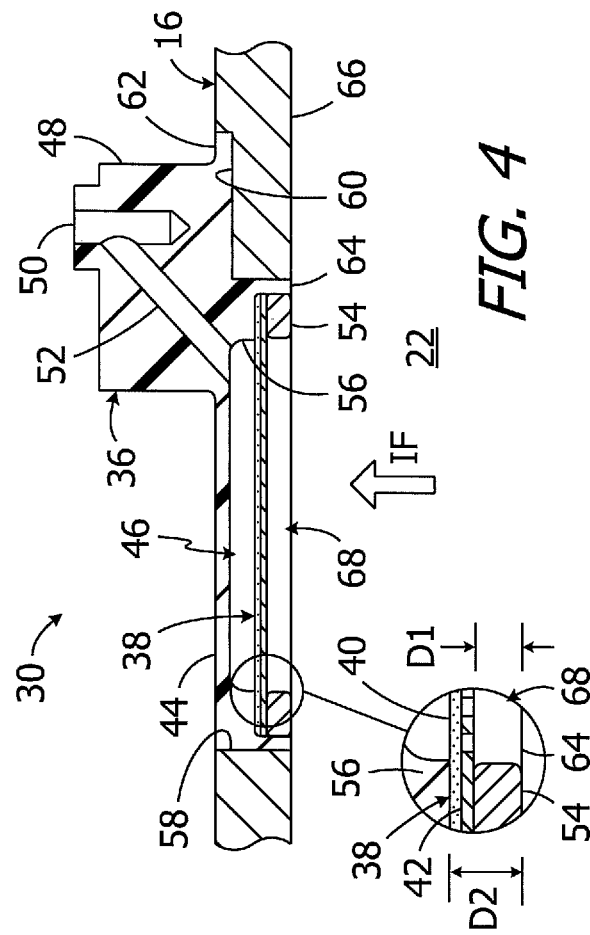
FIG. 4 is a section view of a portion of the implantable infusion device illustrated in FIG. 1.
Figure 3:
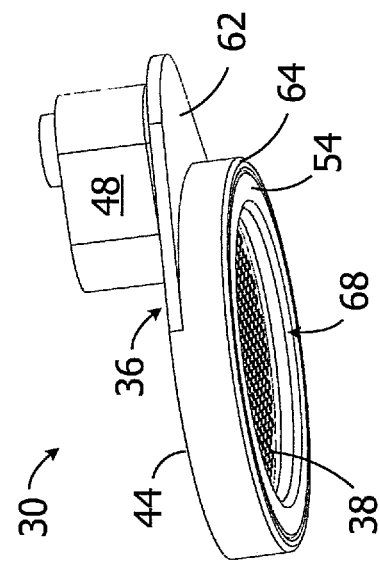
FIG. 3 is perspective view of the filter assembly in the implantable infusion device illustrated in FIG. 1.

Turning to FIGS. 3 and 4, the filter assembly 30 includes a housing 36 and a filter 38 having a bacterial filtration element 40 and a perforated support disk 42 that prevents distortion of the filter element. The filtration element 40 may be a pathogen-blocking bacterial filtration element formed from hydrophilic material that does not pass non-water based liquids or gas. The housing 36 includes a filter portion 44, with a recess 46 for the filter 38, and a connector portion 48 with an outlet lumen 50 that is operably connected to the inlet of the fluid transfer device. A lumen 52 extends from the recess 46 to the outlet lumen 50. The outer perimeter of the filter 38 (i.e., the outer perimeters of the filtration element 40 and support disk 42) is compressed between a support ring 54 and an annular abutment 56 within the recess 46. The support ring 54 may be welded or otherwise secured to the housing filter portion 44.

The internal wall 16 includes an aperture 58 in which the housing filter portion 44 is mounted. The internal wall 16 also includes a recess 60 for the similarly-shaped filter flange 62, which together ensure that that filter housing connector portion 48 is in its intended location within the sealed volume defined by the housing internal wall 16 and cover 18. The respective sizes and configurations of the internal wall 16 and the filter housing 36 results in the free end 64 of the filter housing being flush with the inner surface 66 of the wall 16. Operation of the fluid transfer device causes infusible substance IF within the reservoir internal volume 22 to be draw through the filter 38, recess 46, and lumens 50 and 52, and then into the fluid transfer device inlet. The reservoir convolutes 23 will compress, and the reservoir end wall 24 will move toward the internal wall 16, as the infusible substance is evacuated from the reservoir 20 and the internal volume 22 shrinks.

Although useful, the present inventors have determined that infusion device 10 is susceptible to improvement. One issue is associated with gas bubbles within the reservoir 20 and the configuration of the filter assembly 30. In particular, many infusible substances contain dissolved gases that may evolve from solution and, due to gravity, accumulate and form a bubble at the top region of the reservoir. The region of the reservoir that defines the "top" region will vary based on the orientation of the patient (i.e., standing, sitting, lying down, etc.). With respect to the configuration of the filter assembly 30, and referring to FIGS. 3 and 4, the respective sizes and configurations of the filter housing 36 and filter 38 are such that there is an open, unfilled disk-shaped space (or "pocket") 68 that faces the reservoir internal volume 22. The depth D1 of the pocket 68 is equal to the depth D2 of the portion of the housing recess 46 that extends from the annular abutment 56 to the free end 64, less the thickness of the filter 38. Put another way, the depth D1 of the pocket 68 is equal to distance between the surface of the filter 38 that faces the reservoir and the free end 64 of the housing filter portion 44. The pocket 68 can act as a bubble trap which, as a result of the typical orientation of the infusion device 10 within the patient, will define the highest point within the reservoir when the patient is in a supine position.

The presence of a gas bubble within the pocket 68 and over the filter 38 is problematic because the hydrophilic filter element 40 will be blocked by the bubble. Even a microscopic gas bubble is capable of thinning out, spreading across the entire surface of the wetted filter, thereby preventing the infusible substance from reaching the fluid transfer device. Depending upon the volume of the bubble and negative pressure generated by the pump, the bubble may cover the surface of the support disk 42, and/or fill the perforations of the support disk, and/or or get between the bacterial filtration element 40 and the support disk and cover the reservoir-facing surface of the filtration element. In those instances where the fluid transfer is capable of generating enough force to draw a bubble through the filter 38, certain types of fluid transfer devices (e.g., electromagnet pumps) will experience vapor lock. Moreover, given the depth of the pocket 68 and other factors (e.g., surface tension), the bubble may not float out of the pocket in response to movement and/or reorientation of the patient.

There are also other instances, based on patient orientation and reservoir volume, where the bubble may enter the filter assembly pocket 68. For example, the liquid volume to bubble volume ratio will be relatively large, and the bubble will tend to remain within the bellows convolutes 23, when the reservoir is relatively full (FIG. 2). As the reservoir 20 is depleted, the bubble may be squeezed out of reservoir convolutes 23, and towards the filter assembly 30. A bubble may also simply migrate along the inner surface 66 of the wall 16 toward the filter assembly 30, regardless of reservoir volume, in response to changes in patient (and infusion device) orientation. The present inventors have determined that, in either case, the fact that the free end 64 of the filter housing 44 is flush with the inner surface 66 of the wall 16 increases the likelihood that the bubble will enter the pocket 68.

One example of an implantable infusion device in accordance with at least some of the present inventions is generally represented by reference numeral 100 in FIGS. 5-8. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, a divider wall 106, and a cover 108. An infusible substance (e.g. medication) may be stored in a reservoir 110 that is located within the housing bottom portion 104. The reservoir 110 may be replenished by way of a fill port 112 that extends from the reservoir, through the divider wall 106, to the cover 108. A hypodermic needle (not shown), which is configured to be pushed through the fill port 112, may be used to replenish the reservoir 110. An inlet side safety valve 114, closes when the pressure within the reservoir reaches a predetermined level, may be located between reservoir 110 and the fill port 112.

A wide variety of reservoirs may be employed. In the illustrated embodiment, the reservoir 110 is in the form of a titanium bellows with convolutes 116 and an end wall 118 that is positioned within a sealed volume 120 defined by the housing bottom portion 104 and divider wall 106. The remainder of the sealed volume is occupied by propellant (not shown), which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 100 illustrated in FIGS. 5-8 also includes a fluid transfer device 122 which, in the illustrated implementation, is an electromagnet-pump-based fluid transfer device. Although the present inventions are not so limited, various examples of suitable fluid transfer devices are illustrated and described in U.S. Pat. No. 8,740,861, which is incorporated by reference. The inlet of the fluid transfer device 122 is coupled to the interior 124 (FIGS. 9 and 12) of the reservoir 110 by a filter assembly 126 that is connected to an inlet tube associated with the fluid transfer device 122. The outlet of the fluid transfer device is coupled to an outlet port 128 by a passageway 130 that defines a path from the fluid transfer device to the outlet port. Operation of the fluid transfer device 100 causes infusible substance to move from the reservoir 110 to the infusion device outlet port 128. A catheter 132 may be connected to the outlet port 128 so that the infusible substance passing through the outlet port will be delivered to a target body region in spaced relation to the infusion device 100 by way of the outlet(s) 134 at or near the end of the catheter.

Energy for the fluid transfer device 122, as well for other aspects of the exemplary infusion device 100, is provided by the battery 136 illustrated in FIG. 6. In the specific case of the fluid transfer device 100, the battery 136 is used to charge one or more capacitors 138, and is not directly connected to the fluid transfer device itself. The capacitor(s) 138 are connected to an electromagnet coil in the fluid transfer device 122, and disconnected from the battery 136, when the electromagnet coil is being energized, and are disconnected from the electromagnet coil and connected to the battery when the capacitor(s) are being recharged and/or when the fluid transfer device is at rest. The capacitor(s) 138 are carried on a board 140. A communication device 142, which is connected to an antenna (not shown), is carried on the same side of the board 140 as the capacitor(s) 138. The exemplary communication device 142 is an RF communication device. Other suitable communication devices include, but are not limited to, oscillating magnetic field communication devices, static magnetic field communication devices, optical communication devices, ultrasound communication devices and direct electrical communication devices.

A controller 144 (FIG. 8), such as a microprocessor, microcontroller or other control circuitry, is carried on the other side of the board 140. The controller 144 performs the function of controlling the operations of the infusion device 100 in accordance with instructions stored in memory 145 and/or provided by an external device (e.g. a remote control programmer) by way of the communication device 142. For example, the controller 144 may be used to control the fluid transfer device 122 to supply fluid to the patient in accordance with, for example, a stored basal delivery profile or a bolus delivery request. The controller 144 may also be used to monitor sensed pressure and to perform various analytical and corrective functions.

Referring to FIGS. 5, 6 and 8, the exemplary infusion device 100 is also provided with a side port 146 that is connected to the passageway 130 between the outlet of the fluid transfer device 122 and the outlet port 128. The side port 146 facilitates access to an implanted catheter 132, typically by way of a hypodermic needle. The outlet port 128, a portion of the passageway 130, the antenna (not shown) and the side port 146 are carried by a header assembly 148. The header assembly 148 is a molded, plastic structure that is secured to the housing 102.

The exemplary infusion device 100 illustrated in FIGS. 5-8 also includes a pressure sensor 150 that is connected to the passageway 130 between the outlet of the fluid transfer device 122 and the outlet port 128. The pressure sensor 150 is connected to the controller 144 and may be used to analyze a variety of aspects of the operation of the exemplary implantable infusion device 100. For example, pressure measurements may be used by the controller 144 to determine whether or not there is a blockage in the catheter 132 and whether or not the fluid transfer device 122 is functioning properly. The controller 144 may perform a variety of different functions in response to a determination that the fluid transfer device 122 is not functioning properly or a determination that the catheter 132 is blocked. For example, the controller 144 may actuate an audible alarm 152 that is located within the housing 102 in order to signal that the fluid transfer device 122 is not functioning properly or the catheter 132 is blocked. The controller 144 may also be used to determine, based on the pressure sensed by the pressure sensor 150, whether there is a blockage.

Turning to FIGS. 9-12, the exemplary filter assembly 126 includes a housing 154 and a filter 156 having a hydrophilic bacterial filter element 158 and a perforated support disk 160 (or other liquid permeable filter support) that prevents distortion of the filter element. Suitable materials for the filter element 158 and other filter elements discussed herein include, but are not limited to polysulfone, polyvinylidene fluoride, and cellulose with a thickness of about 125 μm to 200 μm, while suitable materials for the perforated disk 160 and other perforated disks discussed herein include, but are not limited to, titanium, stainless steel, polysulfone with a thickness of about 0.1 mm to 5 mm. The disk perforations 161, which extend completely through the disk 160, may be about 0.01 mm to 1 mm in diameter. The perforated disk 160 may be secured to the housing by press fitting, welding, or any other suitable process or instrumentality. Other exemplary filters are described below with reference to FIGS. 13-25.

The exemplary housing 154 includes a filter portion 162, with a recess 164 for the filter 156, and a connector portion 166 with an outlet lumen 168 that is operably connected to the inlet of the fluid transfer device 122. A lumen 170 extends from the recess 164 to the outlet lumen 168. The support disk 160 is pressed into the filter recess of the housing 154, and the outer perimeter of the filter element 158 is compressed between the outer perimeter of the support disk and an annular abutment 172 within the recess 164. The divider wall 106 includes an aperture 174 in which the housing filter portion 162 is mounted as well as a recess 176 for the similarly-shaped filter flange 178, which together ensure that that filter housing connector portion 166 is in its intended location adjacent to the inlet of the fluid transfer device 122.

Referring more specifically to FIG. 12, the thickness T of the exemplary filter 156 (i.e., the combined thickness of the filter element 158 and perforated support disk 160) may be at least equal to the depth D2 of the portion of the housing recess 164 that extends from the annular abutment 172 to the housing filter portion free end 180 and defines the filter supporting volume. The filter 158, at a minimum, occupies the entire volume of the portion of the housing recess 164 that extends from the annular abutment 172 to the free end 180. As a result, the filter assembly 126 does not have a pocket similar to the pocket 68 of the filter assembly 30 (FIGS. 3 and 4) that can act as a bubble trap. In the illustrated implementation, the thickness T is slightly greater than the depth D2, but the thickness T can be the same as the depth D2 in other implementations.

It should also be noted that the free end 180 of the housing filter portion 162 is not flush with the inner surface 182 of the divider wall 106 in the illustrated implementation. The free end 180 is instead offset the inner surface 182, which faces and defines a border of the reservoir interior 124, by a distance D3 of about 0.1 mm to 1.0 mm and projects into the reservoir interior by the distance D3. The part of the housing filter portion 162 that extends beyond the inner surface 182 acts as a barrier, or fence, that will impede a bubble within the reservoir interior that is moving along the inner surface of the divider wall 106 prior to the bubble reaching the filter 156.

Turning to FIG. 9, the filter assembly 126 is not located adjacent to the reservoir convolutes 116. As such, a bubble squeezed out of reservoir convolutes 116 and towards the filter assembly 126, as the reservoir interior 124 is depleted, will be less likely to reach the filter assembly and cover the filter 156. The inner surface 182 of the divider wall 106 may also include one or more channels, such as channels 185 and 187, which prevent the bellows end wall 118 from sticking to the divider wall 106 when the reservoir is empty.

Figure 13:
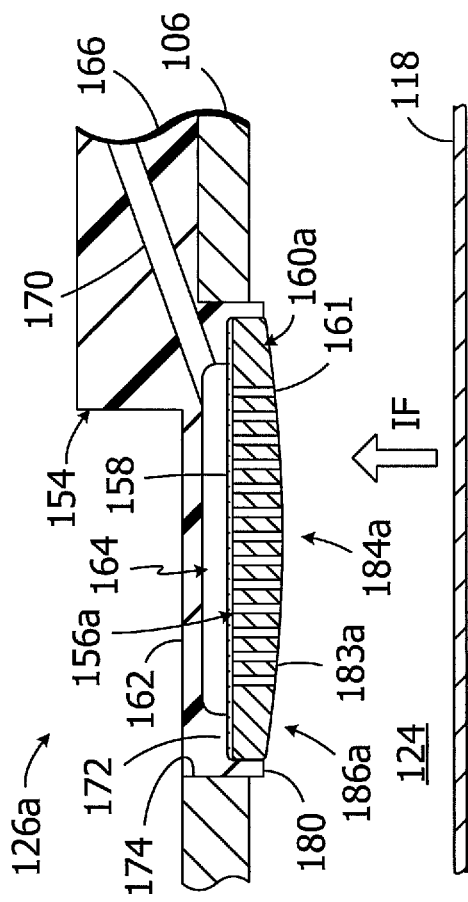
FIG. 13 is a section view of a portion of an implantable infusion device in accordance with one embodiment of a present invention.

Another exemplary filter assembly is generally represented by reference numeral 126a in FIG. 13. The exemplary filter assembly 126a is substantially similar to filter assembly 126 and similar elements are represented by similar reference numerals. For example, the filter assembly 126a may be incorporated into the exemplary infusion device 100 in place of the filter assembly 126. The filter includes a filter element 158 and a support disk 160a. The filter 156a also occupies (at a minimum) the entire portion of the housing recess 164 that extends from the annular abutment 172 to the free end 180 and, as a result, the filter assembly 126a does not have a bubble-trapping pocket similar to the pocket 68 of the filter assembly 30 (FIGS. 3 and 4).

Here, however, the end surface 183a of the exemplary filter 156a that faces the reservoir interior 124 is configured such that the central region 184a of the end surface extends farther than the outer perimeter region 186a of the end surface. Put another way, the end surface central region 184a is closer to the bellows end wall 118 than is the end surface outer perimeter 186a. As a result, the portion of the end surface 183a through which the perforations 161 extend will not be the high point within the reservoir 110 when the infusion device is the orientation illustrated in FIG. 13, and the bubble will be less likely to come to rest over the perforations. The filter end surface 183a, which is the end surface support disk 160a in the illustrated embodiment, may have convex shape (as shown), a conical shape, or any other suitable symmetric or asymmetric shape. Additionally, although the point of greatest extension is at the center of the end surface 183a, the point of greatest extension may also be offset from the center in other implementations.

Figure 14:
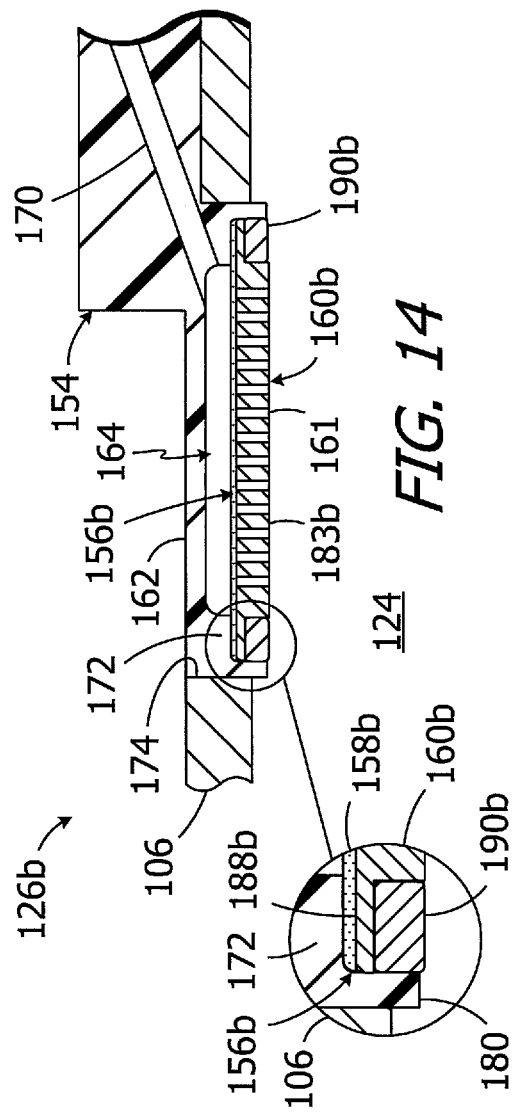
FIG. 14 is a section view of a portion of an implantable infusion device in accordance with one embodiment of a present invention.
Figure 20:
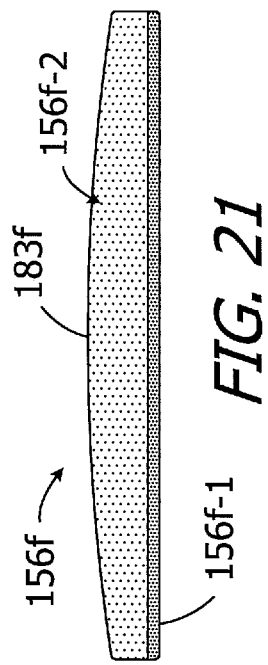
FIG. 20 is a perspective view of a filter in accordance with one embodiment of a present invention.
Figure 21:
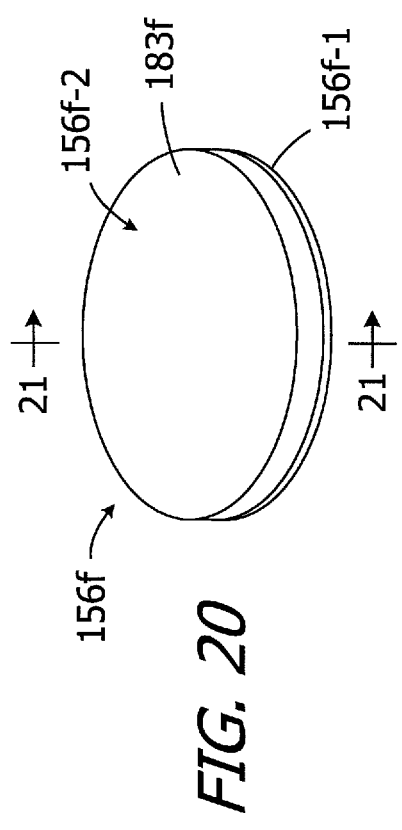
FIG. 21 is a section view taken along line 21-21 in FIG. 20.
Figure 22:
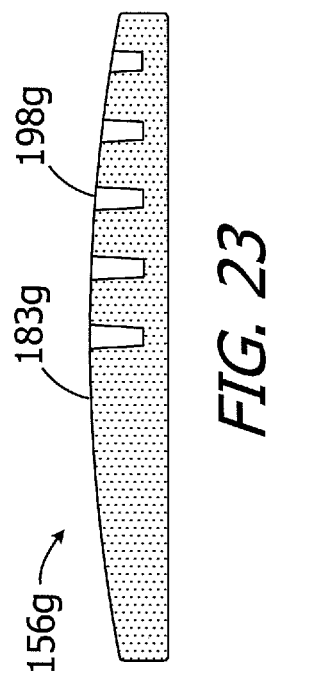
FIG. 22 is a perspective view of a filter in accordance with one embodiment of a present invention.
Figure 23:
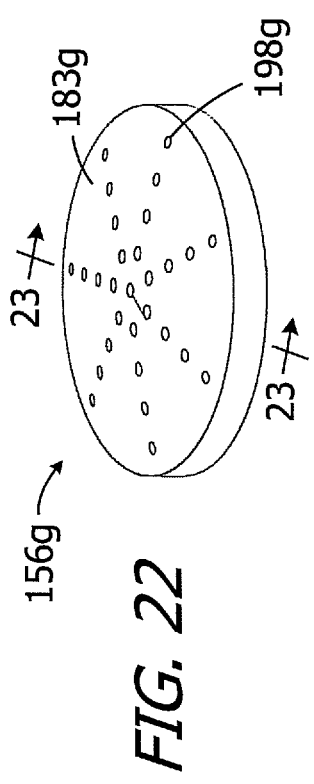
FIG. 23 is a section view taken along line 23-23 in FIG. 22.
Figure 24:
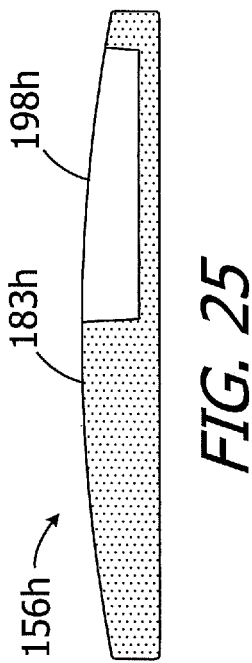
FIG. 24 is a perspective view of a filter in accordance with one embodiment of a present invention.
Figure 25:
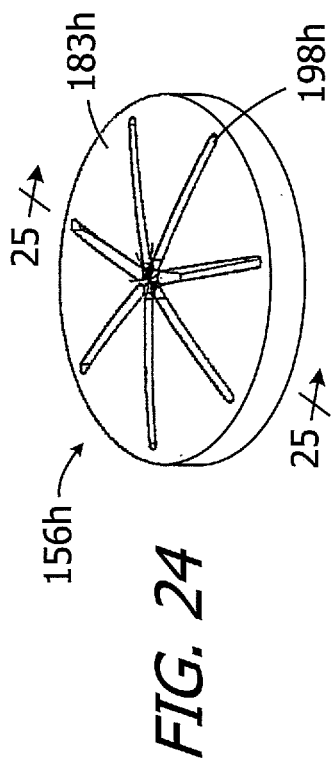
FIG. 25 is a section view taken along line 25-25 in FIG. 24.

Turning to FIG. 14, the exemplary filter assembly 126b is substantially similar to filter assembly 126 and similar elements are represented by similar reference numerals. For example, the filter assembly 126b may be incorporated into the exemplary infusion device 100 in place of the filter assembly 126. The filter 156b, which includes a filter element 158b and a perforated support disk 160b, also occupies (at least) the entire portion of the housing recess 164 that extends from the annular abutment 172 to the free end 180 and, as a result, the filter assembly 126b does not have a bubble-trapping pocket similar to the pocket 68 of the filter assembly 30 (FIGS. 3 and 4).

Here, however, the filter support disk support disk 160b includes an annular flange 188b that is aligned with the annular abutment 172. The outer perimeter of the filter 156b (i.e., the outer perimeter of the filtration element 158 and the annular flange 188b) is compressed between a support ring 190b and the annular abutment 172. The support ring 190b may be welded, press-fit, or otherwise secured to the housing filter portion 162. It should also be noted that the filter end surface 183b, which is the end surface support disk 160b in the illustrated embodiment, may be flat (as shown) or may have convex shape, a conical shape, or any other suitable shape.

Although some filters, such as the exemplary filters described above with reference to FIGS. 9-14, may include separate filter elements and perforated support disks that are placed adjacent to one another during assembly of the associated filter assembly, the present inventions are not so limited. To that end, and referring to FIG. 15, the exemplary filter assembly 126c is substantially similar to filter assembly 126 and similar elements are represented by similar reference numerals. For example, the filter assembly 126c may be incorporated into the exemplary infusion device 100 in place of the filter assembly 126. The filter 156c also occupies (at least) the entire portion of the housing recess 164 that extends from the annular abutment 172 to the free end 180 and, as a result, the filter assembly 126b does not have a bubble-trapping pocket similar to the pocket 68 of the filter assembly 30 (FIGS. 3 and 4).

Here, however, the filter 156c is an integrated, unitary structure that consists of a hydrophilic membrane that is laminated to one or more layers of support material. Exemplary hydrophilic membrane may be formed from materials such as polysulfone, while exemplary support materials include woven or non-woven polypropylenes and polyesters or a calendered support. The filter end surface 183c may be flat (as shown) or may have convex shape, a conical shape, or any other suitable shape. The outer perimeter of the filter 156c is compressed between a support ring 190c and the annular abutment 172. The support ring 190c, may be welded, press-fit, or otherwise secured to the housing filter portion 162, includes an outer portion 192c and a flange 194c that extends inwardly from the outer portion.

The exemplary filter assembly generally represented by reference numeral 126d in FIG. 16 is substantially similar to filter assembly 126 and similar elements are represented by similar reference numerals. For example, the filter assembly 126d may be incorporated into the exemplary infusion device 100 in place of the filter assembly 126. The filter 156d also occupies (at least) the entire portion of the housing recess 164 that extends from the annular abutment 172 to the free end 180 and, as a result, the filter assembly 126d does not have a bubble-trapping pocket similar to the pocket 68 of the filter assembly 30 (FIGS. 3 and 4).

Here, however, the filter 156d includes a filter element 158, a relatively thin support disk 160d, and a liquid absorbent member 196d. The liquid absorbent member 196d stores the infusible substance. In those instances where the exposed surface of the filter assembly 126d is completely covered by a bubble, i.e., when the liquid absorbent member 196d is covered by a bubble, the infusible substance stored in the liquid absorbent member will be drawn through the filter element 158 and support disk 160d, and into the fluid transfer device 122. Suitable materials for the liquid absorbent member 196d include, but are not limited to hydrophilic sponge materials, polyurethane, and cellulose.

The filter end surface 183d (which is the end surface of the liquid absorbent member 196d) may be flat or may have convex shape (as shown), a conical shape, or any other suitable shape. The outer perimeter of the filter 156d is compressed between a support ring 190d and the annular abutment 172. The support ring 190d may be welded, press-fit, or otherwise secured to the housing filter portion 162. In some instances, the outer perimeter of the liquid absorbent member 196d may include a thin flange that is compressed between the support ring 190d and the annular abutment 172.

It should also be noted that, in some instances, the free end of the housing filter portion may simply be flush with the inner surface of the divider wall. To that end, and referring to FIG. 17, the relative dimensions of the divider wall 106' and the filter assembly 126b are such that the free end 180 of the housing filter portion 162 is flush with the divider wall inner surface 182.

Another exemplary filter assembly is generally represented by reference numeral 126e in FIG. 18. Filter assembly 126e is substantially similar to filter assembly 126a and similar elements are represented by similar reference numerals. For example, the filter assembly 126e may be incorporated into the exemplary infusion device 100 in place of the filter assembly 126. The filter 156e occupies (at least) the entire portion of the housing recess 164 that extends from the annular abutment 172 to the free end 180 and, as a result, the filter assembly 126e does not have a bubble-trapping pocket similar to the pocket 68 of the filter assembly 30 (FIGS. 3 and 4). The filter 156e may also have the end surface 183e that faces the reservoir interior 124 is configured such that the central region 184e extends farther than the outer perimeter region 186e (as shown) or may have a flat end surface. The end surface 183e may have convex shape (as shown), a conical shape, or any other suitable symmetric or asymmetric shape.

Here, however, the filter 156e is one-piece, unitary structure that is formed from porous sintered titanium (or other porous sintered metal). The filter 156e has an absolute filter rating (or "filter rating") of 0.2 µm in the illustrated implementation, i.e., the filter will block particles that are 0.2 µm or larger. The filter rating is consistent throughout the filter 156e. In other implementations, the filter rating may vary from the end surface 183e to the opposite surface and/or from the central region 184e to the outer perimeter region 186e. To that end, the exemplary filter 156f, which may be used in place of the filter 156e in the filter assembly 126e, includes a first filter layer 156f-1 with a filter rating of 0.2 µm and a second filter layer 156f-2 with a filter rating of 2.0 µm. In other implementations, the filter rating variation may be gradual over the entire thickness, as opposed to the use of two distinct layers having different filter ratings.

The sintered titanium filters 156e and 156f illustrated in FIGS. 18-21 have smooth (but for the pores) reservoir facing surfaces 183e and 183f. Other filter implementations, which may be used in place of the filter 156e in the filter assembly 126e, include surface features that decrease the likelihood that a bubble which reaches the reservoir facing surface will conform to the entire surface and block the filter. By way of example, but not limitation, the filter 156g (FIGS. 22 and 23) includes a plurality of apertures 198g that extend through the surface 183g, while the filter 156h (FIGS. 24 and 25) includes a plurality of slots 198h that extend through the surface 183h. The apertures 198g and slots 198h extend only partially through the filters 156g and 156h.

The filters 156e to 156h may be secured to the housing 154 by, for example, press fitting and/or laser welding, and in many instances without the use of a support ring. With respect to manufacturing, the filters 156e to 156h may be formed by known sintering processes, such as mold-based sintering and selective laser sintering. Surface features such as the apertures 198g and slots 198h may also be formed in a smooth sintered filter (such as that illustrated in FIGS. 18 and 19) through the use of laser engraving or other suitable techniques.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. Moreover, the inventions include any and all combinations of the elements from the various embodiments disclosed in the specification. It is intended that the scope of the present inventions extend to all such modifications and/or additions and that the scope of the present inventions is limited solely by the claims set forth below.

We claim:

1. An ambulatory infusing device, comprising:
   a housing;
   a reservoir defining an interior volume;
   a wall associated with the housing and having an inner surface that faces into the reservoir interior volume; and
   a filter assembly including
      a filter assembly housing with a housing filter portion having a free end associated with the inner surface of the wall and a filter supporting volume that extends to the free end of the housing filter portion,
      a filter located within the filter supporting volume that extends to at least the free end of the housing filter portion, and
      a liquid absorbent member, and
   a pump-based fluid transfer device operably connected to the reservoir interior volume by way of the filter assembly;
   wherein the folter comprises a filter element and a liquid permeable filter support.

2. An ambulatory infusing device as claimed in claim 1, wherein the filter element comprises a hydrophilic membrane.

3. An ambulatory infusing device as claimed in claim 1, wherein the liquid permeable filter support comprises a perforated disk.

4. An ambulatory infusing device as claimed in claim 1, wherein the filter element is laminated to the liquid permeable filter support.

5. An ambulatory infusing device, comprising:
a housing;
a reservoir defining an interior volume;
a wall associated with the housing and having an inner surface that faces into the reservoir interior volume; and
a filter assembly including
a filter assembly housing with a housing filter portion having a free end associated with the inner surface of the wall and a filter supporting volume that extends to the free end of the housing filter portion,
a filter located within the filter supporting volume that extends to at least the free end of the housing filter portion, and
a liquid absorbent member, and
a pump-based fluid transfer device operably connected to the reservoir interior volume by way of the filter assembly;
wherein the filter comprises a hydrophilic membrane that is laminated to one or more layers of support material.

6. An ambulatory infusing device as claimed in claim 1, wherein the filter comprises a sintered metal filter.

7. An ambulatory infusing device as claimed in claim 6, wherein the metal comprises titanium.

8. An ambulatory infusing device as claimed in claim 6, wherein the sintered metal filter includes a plurality of surface features that extend partially through the filter.

9. An ambulatory infusing device as claimed in claim 6, wherein different portions of the sintered metal filter define different filter ratings.

10. An ambulatory infusing device, comprising:
a housing;
a reservoir defining an interior volume;
a wall associated with the housing and having an inner surface that faces into the reservoir interior volume; and
a filter assembly including
a filter assembly housing with a housing filter portion having a free end associated with the inner surface of the wall and a filter supporting volume that extends to the free end of the housing filter portion,
a filter located within the filter supporting volume that extends to at least the free end of the housing filter portion, and
a liquid absorbent member, and
a pump-based fluid transfer device operably connected to the reservoir interior volume by way of the filter assembly;
wherein the filter defines an end surface, including a central region and an outer perimeter region, that faces the reservoir interior volume and the central region of the end surface includes one or more perforations and extends farther than the outer perimeter region of the end surface into the reservoir interior volume.

11. An ambulatory infusing device as claimed in claim 1, wherein the filter defines a flat end surface that faces the reservoir interior volume.

12. An ambulatory infusing device as claimed in claim 1, wherein the free end of the filter assembly housing filter portion extends beyond the inner surface of the wall.

13. An ambulatory infusing device as claimed in claim 1, wherein the free end of the filter assembly housing filter portion is flush with the inner surface of the wall.

14. An ambulatory infusing device as claimed in claim 1, wherein the reservoir comprises a bellows reservoir.

15. An ambulatory infusing device as claimed in claim 1, wherein the pump-based fluid transfer device is operably connected between the filter assembly and an outlet port of the ambulatory infusing device.

16. An ambulatory infusing device as claimed in claim 1, wherein the pump-based fluid transfer device comprises an electromagnet pump-based fluid transfer device.

17. An ambulatory infusing device as claimed in claim 1, wherein the liquid absorbent member is formed from a material selected from the group consisting of hydrophilic sponge materials, polyurethane, and cellulose.

* * * * *